US012740697B2

(12) United States Patent
Li

(10) Patent No.: US 12,740,697 B2
(45) Date of Patent: Sep. 22, 2026

(54) SHORT-WAVE INFRARED BASED IMAGING

(71) Applicant: Cision Vision, Inc., Mountain View, CA (US)

(72) Inventor: Zhongming Li, Sunnyvale, CA (US)

(73) Assignee: Cision Vision, Inc., Mountain View, CA (US)

( * ) Notice: Subject to any disclaimer, the term of this patent is extended or adjusted under 35 U.S.C. 154(b) by 369 days.

(21) Appl. No.: 18/253,553

(22) PCT Filed: Nov. 18, 2021

(86) PCT No.: PCT/US2021/059902
§ 371 (c)(1),
(2) Date: May 18, 2023

(87) PCT Pub. No.: WO2022/109143
PCT Pub. Date: May 27, 2022

(65) Prior Publication Data

US 2024/0008733 A1 Jan. 11, 2024

Related U.S. Application Data

(60) Provisional application No. 63/115,945, filed on Nov. 19, 2020.

(51) Int. Cl.
*A61B 1/313* (2006.01)
*A61B 1/04* (2006.01)
(Continued)

(52) U.S. Cl.
CPC ............ *A61B 1/3132* (2013.01); *A61B 1/046* (2022.02); *A61B 1/0638* (2013.01); *A61B 1/07* (2013.01)

(58) Field of Classification Search
CPC ..... A61B 1/00126; A61B 1/042; A61B 1/046; A61B 1/0638; A61B 1/0646; A61B 1/0669
See application file for complete search history.

(56) References Cited

U.S. PATENT DOCUMENTS 7,179,222 B2 2/2007 Imaizumi
11,382,487 B2 * 7/2022 Frangioni ........ A61B 1/000094
(Continued)

FOREIGN PATENT DOCUMENTS

EP 3705022 A1 9/2020
JP H4-229816 A 8/1992
(Continued)

OTHER PUBLICATIONS

Examination Report dated Jun. 20, 2025, directed to EP Application No. 21895592.0; 4 pages.
(Continued)

*Primary Examiner* — Michael J Carey
*Assistant Examiner* — Stephen Floyd London
(74) *Attorney, Agent, or Firm* — Morrison & Foerster LLP

(57) ABSTRACT

A system includes a laparoscope including a first port, a second port, and an optical system. The optical system includes a first port coupling, a shortwave infrared (SWIR) sensor coupling configured to couple to a SWIR sensor, and a visible-light sensor coupling configured to couple to a visible-light sensor. The optical system is configured to optically couple to at least the second port of the laparoscope via the first port coupling. The optical system is configured to receive a detection SWIR beam from the second port and direct at least a portion of the detection SWIR beam to the SWIR sensor coupling. The optical system is further configured to receive a detection visible-light beam from the second port and direct at least a portion of the detection visible-light beam to the visible-light sensor coupling.

15 Claims, 5 Drawing Sheets

(51) Int. Cl.
*A61B 1/06* (2006.01)
*A61B 1/07* (2006.01)

(56) References Cited

U.S. PATENT DOCUMENTS

| | | | | |
|---|---|---|---|---|
| 2001/0007920 | A1* | 7/2001 | Hayashi | A61B 1/0005 600/476 |
| 2003/0078477 | A1* | 4/2003 | Kang | A61B 5/0084 600/109 |
| 2006/0184040 | A1 | 8/2006 | Keller et al. | |
| 2012/0268573 | A1* | 10/2012 | Schonborn | A61B 5/0062 348/E13.074 |
| 2012/0310047 | A1* | 12/2012 | Kasamatsu | A61B 1/0638 600/178 |
| 2013/0271768 | A1* | 10/2013 | Takaoka | A61B 1/0669 356/445 |
| 2015/0238071 | A1* | 8/2015 | Hua | A61B 1/3132 600/109 |
| 2015/0287192 | A1 | 10/2015 | Sasaki | |
| 2016/0022126 | A1* | 1/2016 | Ramesh | A61B 1/0638 600/109 |
| 2016/0062103 | A1* | 3/2016 | Yang | A61B 1/07 250/552 |
| 2017/0027448 | A1 | 2/2017 | Carr et al. | |
| 2018/0279864 | A1 | 10/2018 | Frangioni | |
| 2019/0159663 | A1* | 5/2019 | Krstajic | A61B 5/0071 |
| 2019/0298151 | A1 | 10/2019 | Frangioni | |
| 2019/0328206 | A1 | 10/2019 | Muramatsu et al. | |
| 2019/0328216 | A1* | 10/2019 | Beyer | A61B 1/00096 |
| 2020/0026062 | A1 | 1/2020 | Schuster et al. | |
| 2020/0187782 | A1* | 6/2020 | Khan | A61B 5/0035 |
| 2020/0245921 | A1 | 8/2020 | Li et al. | |
| 2023/0032021 | A1* | 2/2023 | Douplik | A61B 1/015 |
| 2023/0309907 | A1 | 10/2023 | Li et al. | |
| 2024/0122529 | A1 | 4/2024 | Li et al. | |
| 2024/0280490 | A1* | 8/2024 | Perry | A61B 1/0638 |

FOREIGN PATENT DOCUMENTS

| | | | |
|---|---|---|---|
| JP | 2004-73647 | A | 3/2004 |
| JP | 2011-251145 | A | 12/2011 |
| WO | 2020/006454 | A1 | 1/2020 |

OTHER PUBLICATIONS

Extended Search Report dated Oct. 22, 2024, directed to EP Application No. 21895592.0; 6 pages.

International Search Report and Written Opinion mailed Feb. 4, 2022, directed to International Application No. PCT/US2021/059902; 12 pages.

* cited by examiner

SHORT-WAVE INFRARED BASED IMAGING

CROSS-REFERENCE TO RELATED APPLICATION(S)

This application is a national stage application under 35 U.S.C. § 371 of International Application No. PCT/US2021/059902, filed Nov. 18, 2021, which claims priority to and the benefit of U.S. Provisional Patent Application No. 63/115,945, filed Nov. 19, 2020, the entire contents of each priority application are incorporated herein by reference.

BACKGROUND

Lymph nodes, also known as lymph glands, are oval-shaped organs that are widely present throughout the human and animal bodies. Lymph node is an integral part of the lymphatic system, which is responsible for the immune responses to protect the body from diseases and infections. The condition of lymph nodes can be directly indicative to one's health conditions. Swollen lymph nodes can be an indication of bacterial infection, virus infection, cancer, etc. Checking the condition of lymph nodes by imaging them is extremely useful to disease diagnosis, prevention, and treatment.

Currently, there are a number of imaging modalities to visualize and examine the lymph nodes. Traditionally, the standard method is lymphography. Lymphography involves injecting radiocontrast agents into patients and visualize the lymph nodes and lymphatic vessels with X-ray. This procedure is invasive, causes significant discomfort and involves using radioactive agents. In recent years, cross sectional imaging modalities, including Computational Tomography (CT) and Magnetic Resonance Imaging (MRI), have become increasingly popular, in replacement of lymphography in lymph node visualization. Ultrasound and Positron Emission Tomography (PET) have also been demonstrated to be useful. Although with these techniques mentioned above, doctors are able to identify lymph nodes and make a reasonably accurate judgment of their conditions, they are general-purpose imaging modalities, so their working mechanisms are not designed to give the best contrast for lymph nodes specifically, unless specific contrasting agents are injected. As a result, other organs and tissues show up in these images with the same or sometimes even better contrast compared to lymph nodes, causing distractions to the task of finding and examining the lymph nodes.

SUMMARY

As described above, there are a number of imaging modalities to visualize and examine the lymph nodes. Additionally, medical imaging of other tissue (or non-tissue objects within the body or within tissue) is widely used. However, known medical imaging techniques have several shortcomings, for example their inability to accurately and robustly identify target tissue and/or target features. Accordingly, improved medical imaging methods and systems are needed.

Disclosed herein are systems and methods for providing improved medical imaging, including by providing improved multimodal imaging for capturing medical images of target tissue by simultaneously using multiple wavelengths of light, and including by using laparoscope devices. As described herein, an imaging system may include one or more accessories configured to be attachable to a laparoscope to configure the laparoscope for multimodal imaging using two wavelengths of light, for example visible light and short-wave infrared (SWIR) light.

In some embodiments, a single accessory may be attachable to a laparoscope to enable cross-polarization SWIR imaging and simultaneous white-light imaging. The accessory attached to a port of a laparoscope may use one or more optical elements (e.g., beam-splitters, dichroic mirrors, etc.) to (a) direct a SWIR inspection beam into a central optical path of a laparoscope and to (b) collect both a SWIR detection beam and a visible-light detection beam from the central optical path of the laparoscope, and split the beams from one another such that they are directed to respective optical sensors configured for the respective wavelengths. By transmitting both inspection SWIR light and detection SWIR light on the central optical path of the laparoscope, scattering of the SWIR light as it travels through the laparoscope may be minimized, thereby improving performance of cross-polarization imaging using the laparoscope.

In some embodiments, one or more accessories may be attachable to two ports of a laparoscope to enable cross-polarization SWIR imaging and simultaneous white-light imaging. The one or more accessories may use a first set of one or more optical elements (e.g., beam-splitters, dichroic mirrors, etc.) to splice together a SWIR inspection beam and a visible-light inspection beam and to direct both beams into a first port of the laparoscope and into a peripheral optical path of the laparoscope. The one or more accessories may use second set of one or more optical elements (e.g., beam-splitters, dichroic mirrors, etc.) to collect both a SWIR detection beam and a visible-light detection beam from the central optical path of the laparoscope via a second port of the laparoscope, and to split the beams from one another such that they are directed to respective optical sensors configured for the respective wavelengths. By transmitting both inspection SWIR light and detection visible light on a first single optical path of the laparoscope, and by transmitting both detection SWIR light and detection visible light on a second single optical path of the laparoscope, multimodal imaging using the laparoscope may be performed without requiring parallel optical paths for different wavelengths of light, thereby minimizing the laparoscope diameter.

Various aspects of the disclosed subject matter may provide one or more of the following capabilities.

In one implementation, a system includes a laparoscope including a first port and a second port an optical system. The optical system includes a first port coupling, a short-wave infrared (SWIR) sensor coupling configured to couple to a SWIR sensor, and a visible-light sensor coupling configured to couple to a visible-light sensor. The optical system is configured to optically couple to at least the second port of the laparoscope via the first port coupling. The optical system is configured to receive a detection SWIR beam from the second port and direct at least a portion of the detection SWIR beam to the SWIR sensor coupling. The optical system is further configured to receive a detection visible-light beam from the second port and direct at least a portion of the detection visible-light beam to the visible-light sensor coupling.

One or more of the following features can be included in any feasible combination.

In one implementation, the laparoscope is configured to receive an inspection visible-light beam via the first port, and an inspection SWIR beam via one of the first port and the second port. In another implementation, the optical system includes a SWIR source coupling configured to couple to a SWIR source and receive an input SWIR beam via the SWIR source coupling. The inspection SWIR beam is a portion of the input SWIR beam. In yet another implementation, the detection visible-light beam is generated based on an interaction between a target tissue and at least a portion of the inspection visible-light. The detection SWIR beam is generated based on an interaction between the target tissue and at least a portion of the inspection SWIR beam.

In one implementation, the system includes a first polarizer configured to receive the input SWIR beam, and transmit a first SWIR beam. The first SWIR beam includes a portion of the input SWIR beam and has a first polarization. The optical system further includes a first optical element downstream from the first polarizer and configured to receive the first SWIR beam and transmit at least a portion of the first SWIR beam having the first polarization. The optical system also includes a second optical element configured to receive a second SWIR beam including the portion of the first SWIR beam transmitted by the first optical element, and reflect at least a portion of the second SWIR beam. The inspection SWIR beam includes the at least portion of the second SWIR beam, and is directed out of the optical system via the first port coupling and the second port of the laparoscope. The second optical element is configured to receive the detection visible-light beam and the detection SWIR beam via the first port coupling and the second port, transmit a first visible-light beam including at least a portion of the detection visible-light beam and reflect at least a portion of the detection SWIR beam.

In one implementation, the first optical element is configured to receive a third SWIR beam including the portion of the detection SWIR beam reflected by the second optical element, and reflect at least a portion of the third SWIR beam having a second polarization. In another implementation, the system further includes a second polarizer configured to receive a fourth SWIR beam including the at least a portion of the third SWIR beam reflected by the first optical element, and transmit at least a portion of the fourth SWIR beam, the second polarizer configured to transmit SWIR radiation having the second polarization. In yet another implementation, the at least portion of the fourth SWIR beam is directed out of the optical system via the SWIR sensor coupling. In one implementation, at least a portion of the first visible-light beam is directed out of the optical system via the visible-light sensor coupling. In another implementation, the SWIR beam has a wavelength between 0.9 microns and 2 microns.

In one implementation, the optical system includes a second port coupling configured to couple to the first port of the laparoscope; and a visible-light source coupling configured to couple to a visible-light source, and receive an input visible-light beam via the visible-light source coupling. In another implementation, the optical system includes a first optical sub-system coupled to the second port of the laparoscope, the first optical sub-system includes a first optical element configured to receive the detection visible-light beam and the detection SWIR beam via the first port coupling and the second port; and transmit a first visible-light beam including at least a portion of the detection visible-light beam and reflect at least a portion of the detection SWIR beam.

In one implementation, the first optical sub-system further includes a polarizer configured to receive a first SWIR beam including the at least portion of the detection SWIR beam reflected by the first optical element and transmit a second SWIR beam including at least a portion of the first SWIR beam having a first polarization. In another implementation, at least a portion of the second SWIR beam is directed out of the first optical system via the SWIR sensor coupling. In yet another implementation, at least a portion of the first visible-light beam is directed out of the first optical system via the visible-light sensor coupling. In another implementation, the system further includes a second optical system coupled to the first port of the laparoscope and including a second optical element. The second optical element is configured to receive the input visible-light beam via the visible-light source coupling and reflect at least a portion of the input visible-light beam. The inspection visible-light beam includes the at least portion of the input visible-light beam. The inspection visible-light beam is directed out of the second optical system via the second port coupling and the first port of the laparoscope.

In one implementation, the second optical element is configured receive the input SWIR beam via the SWIR source coupling and transmit at least a portion of the input SWIR light beam. The inspection SWIR beam includes the at least the portion of the input SWIR beam, and the inspection SWIR beam is directed out of the second optical system via the second port coupling and enters the laparoscope via the first port. In another implementation, the laparoscope includes a first optical path configured to optically couple the first port with an output aperture of the laparoscope. The inspection visible-light beam and the inspection SWIR light beam are configured to travel along the first light path; and a second light path is configured to optically couple the output aperture with the second port. Detection visible-light beam and the detection SWIR light beam are configured to travel along the second optical path.

In one implementation, an optical system includes an SWIR source coupling; and a first polarizer configured to receive, via the SWIR source coupling, an input SWIR beam, and transmit a first SWIR beam. The first SWIR beam includes a portion of the input SWIR beam and has a first polarization. The optical system also includes a first optical element downstream from the first polarizer and configured to receive the first SWIR beam and transmit at least a portion of the first SWIR beam having the first polarization. The optical system further includes a second optical element configured to receive a second SWIR beam including the portion of the first SWIR beam transmitted by the first optical element, and reflect at least a portion of the second SWIR beam. An inspection SWIR beam including the at least portion of the second SWIR beam is directed out of the optical system via a first port coupling. The second optical element is configured to receive a detection visible-light beam and a detection SWIR beam via the first port coupling, transmit a first visible-light beam including at least a portion of the detection visible-light beam and reflect at least a portion of the detection SWIR beam.

One or more of the following features can be included in any feasible combination.

In one implementation, the detection SWIR beam is generated based on an interaction between at least a portion of the inspection SWIR beam and a target tissue. In another implementation, the first optical element is configured to receive a third SWIR beam including the portion of the inspection SWIR beam reflected by the second optical element and reflect at least a portion of the third SWIR beam having a second polarization. In another implementation, the optical system further includes a second polarizer configured to receive a fourth SWIR beam including the at least a portion of the third SWIR beam reflected by the first optical element, and transmit at least a portion of the fourth SWIR beam, the second polarizer configured to transmit SWIR radiation having the second polarization.

In one implementation, the at least portion of the fourth SWIR beam is directed out of a SWIR sensor coupling of the optical system. In another implementation, at least a portion of the first visible-light beam is directed out of the optical system via a visible-light sensor coupling of the optical system. In yet another implementation, the first optical element is a polarization beam splitter. In one implementation, the first optical element is an intensity beam splitter.

The present disclosure refers to various beams, including but not limited to an inspection SWIR beam, an inspection visible-light beam, a detection SWIR beam, and a detection visible-light beam. As used herein, an "inspection" beam may include all or any part of a beam generated at a light source and traveling to a target tissue. As used herein, a "detection" beam may include all or any part of a beam generated at target tissue and traveling to a detector. The beams disclosed herein may traverse various optical elements including ports, port connectors, lenses, polarizers, mirrors, beam splitters, fibers, and the like, one or more of which may transmit and/or reflect all or part of the beam. The beams disclosed herein may include various "portions" that form part of the beam, wherein a portion of a beam may constitute a spatial portion of the beam (e.g., constituting a length between two points on the beam's path) and/or a portion of the beam in polarization-space. A person of skill in the art will understand that different portions of a beam may be referred to as separate beams and/or as portions of a single overall beam.

Non-transitory computer program products (i.e., physically embodied computer program products) are also described that store instructions, which when executed by one or more data processors of one or more computing systems, causes at least one data processor to perform operations herein. Similarly, computer systems are also described that may include one or more data processors and memory coupled to the one or more data processors. The memory may temporarily or permanently store instructions that cause at least one processor to perform one or more of the operations described herein. In addition, methods can be implemented by one or more data processors either within a single computing system or distributed among two or more computing systems. Such computing systems can be connected and can exchange data and/or commands or other instructions or the like via one or more connections, including a connection over a network (e.g. the Internet, a wireless wide area network, a local area network, a wide area network, a wired network, or the like), via a direct connection between one or more of the multiple computing systems, etc.

These and other capabilities of the disclosed subject matter will be more fully understood after a review of the following figures, detailed description, and claims.

BRIEF DESCRIPTION OF THE FIGURES

These and other features will be more readily understood from the following detailed description taken in conjunction with the accompanying drawings, in which.

DETAILED DESCRIPTION

Surgical imaging instruments (e.g., laparoscopes, endoscopes, etc.) are often used to image biological tissues. Typically, surgical imaging instruments are designed to operate at visible-light wavelengths (e.g., 380 nanometers (nm)-850 nm). Imaging using only visible-light may not provide sufficient contrast between a biological tissue and the surrounding tissues. Short-wave infrared (SWIR) radiation can provide desirable contrast between tissues (e.g., lymph nodes, lymphatic vessels, blood vessels, etc.) and the surrounding tissues. Therefore, it can be desirable to develop imaging surgical systems that can image a tissue using SWIR radiation or a combination of SWIR radiation and visible-light. Some implementations of the current subject matter provide for optical systems that facilitate imaging of tissues at SWIR wavelengths or a combination of SWIR and visible-light wavelengths. In some implementations, the optical systems can be retrofitted on existing surgical imaging instruments (e.g., laparoscopes). This can enhance the capability of the surgical imaging instrument by allowing it to perform SWIR imaging.

Figure 1:
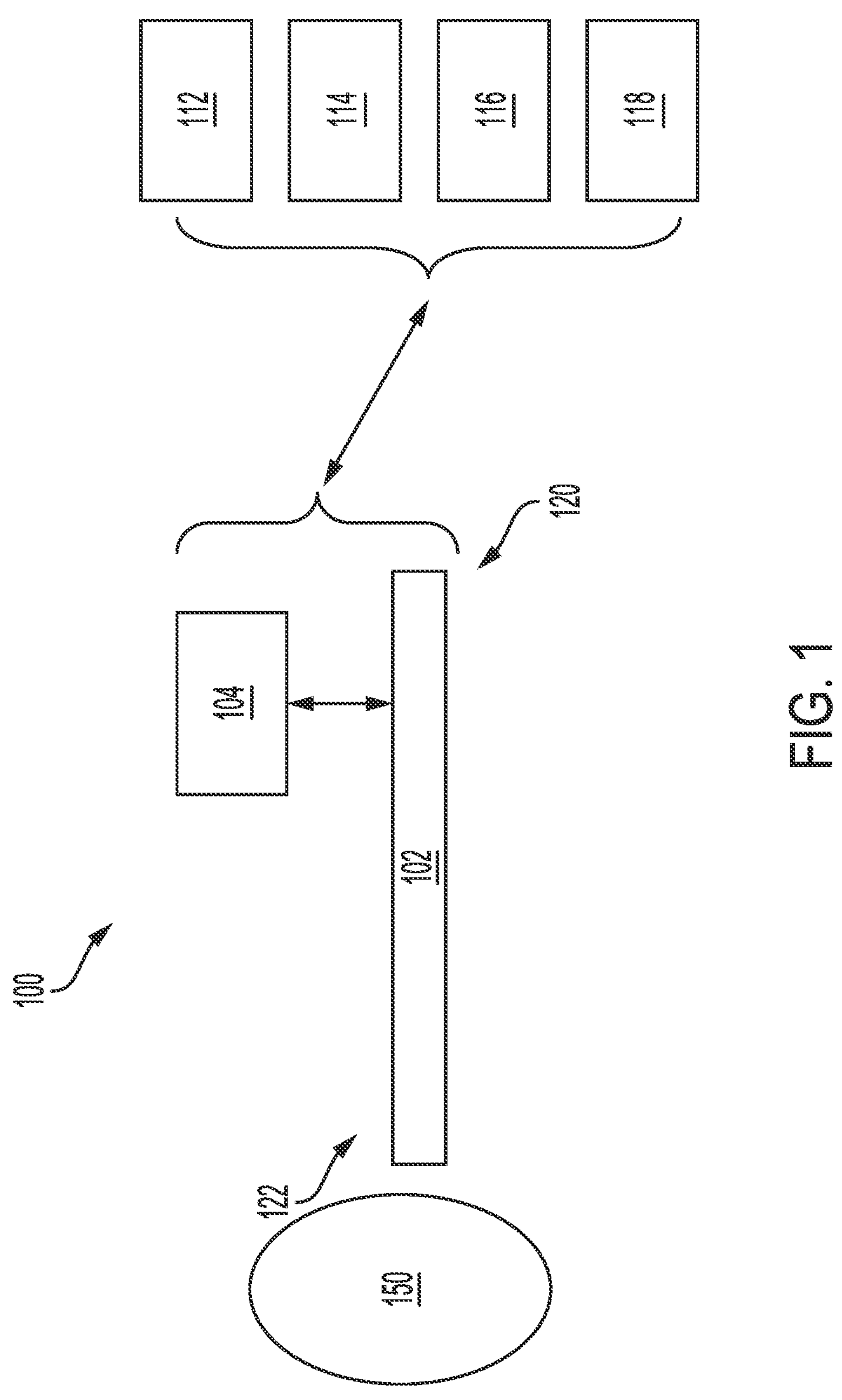
FIG. 1 illustrates a schematic illustration of an exemplary imaging system configured to image a target tissue.

FIG. 1 illustrates a schematic illustration of an exemplary imaging system 100 including a laparoscope 102 and an optical system 104, and configured to image a target tissue 150. The imaging system 100 can be in optical communication with optical sources (e.g., lasers emitting visible-light, SWIR, etc.) and optical sensors. For example, the imaging system can receive a visible-light beam from a visible-light source 112, and/or a SWIR beam from a SWIR light source 114. The visible-light beam and/or SWIR beams can be transmitted to the target tissue 150 by the laparoscope from the proximal end 120 to a distal end 122, and can be used to perform an inspection (e.g., imaging) of the target tissue 150. Detection beams that are generated based on the interaction of the visible-light beam and/or SWIR beams can be transmitted by the laparoscope 102 from the distal end 122 to the proximal end 120. For example, a detection visible-light beam (generated based on interaction of visible-light beam and the target tissue 150) can be transmitted to a visible-light detector 116, and/or a detection SWIR beam (generated based on interaction of SWIR beam and the target tissue 150) can be transmitted to a SWIR detector 118.

The optical system 104 can be optically coupled to the laparoscope 102 via one or more ports on the laparoscope 102. The optical system 104 can modify the visible-light beam/SWIR beam generated by the visible-light source 112/SWIR light source 114 prior to transmission through the laparoscope (e.g., change polarization). The optical system 104 can behave like an optical filter. In some implementations, the optical system can be a long pass filter (e.g., attenuates shorter wavelengths and transmits longer wavelengths). In some implementations, the optical system can be a short pass filter (e.g., attenuates longer wavelengths and transmits shorter wavelengths). In some implementations, the optical system can be a band pass filter (e.g., transmits a predetermined range of wavelengths and attenuates wavelengths outside the predetermined range). The optical system 104 can modify the detection visible-light beam/detection SWIR beam (e.g., change polarization) prior to their detection. Additionally or alternately, the optical system can behave as a long pass filter, short pass filter, band pass filter for the detection visible-light/detection SWIR beams.

Below, FIGS. 2 and 3 describe some embodiments of imaging systems and components thereof for laparoscopic imaging. In particular, the systems described may enable cross-polarization SWIR imaging using an accessory that may be attached to a port of a laparoscope, wherein the accessory uses one or more optical elements (e.g., beam-splitters, dichroic mirrors, etc.) to (a) direct a SWIR inspection beam into a central optical path of a laparoscope and to (b) collect both a SWIR detection beam and a visible-light detection beam from the central optical path of the laparoscope, and split the beams from one another such that they are directed to respective optical sensors configured for the respective wavelengths.

Figure 2:
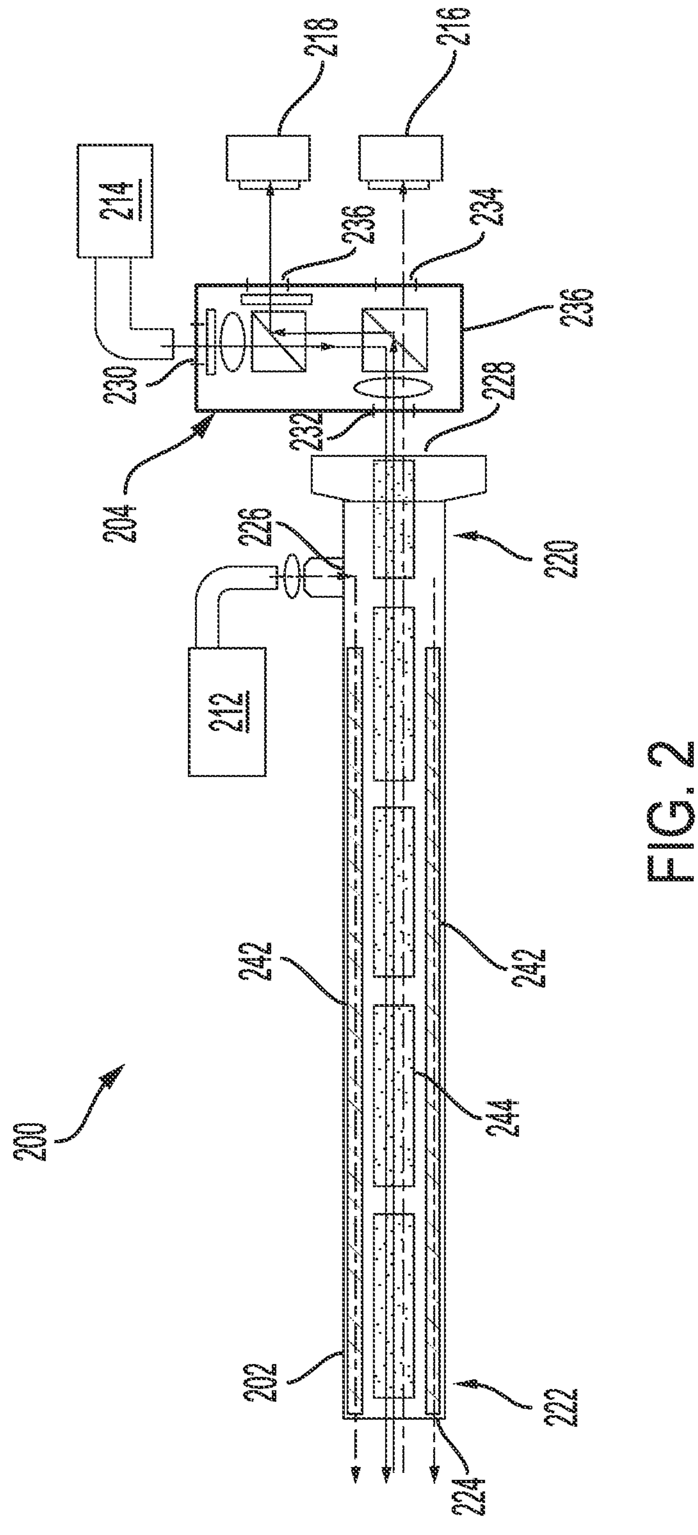
FIG. 2 illustrates an exemplary embodiment of a short-wave infrared (SWIR) imaging system.

FIG. 2 illustrates an exemplary embodiment of an imaging system 200. The imaging system 200 includes a laparoscope 202 and an optical system 204. The imaging system 200 can be optically coupled with a visible-light source 212 and a SWIR source 214. The imaging system 200 can be optically coupled to visible-light detector 216 and SWIR detector 218. The laparoscope 202 can guide inspection beams (e.g., visible-light beam, SWIR beams, etc.) that can exit via an output aperture 224 of the laparoscope 202.

The laparoscope 202 can include a first port 226 and a second port 228. The first port 226 of the laparoscope 202 can receive an input visible-light beam from the visible-light source 212. The inspection visible-light beam or a portion thereof (referred to as inspection visible-light beam) can be transmitted by the laparoscope from the proximal end 220 to the distal end 222. The second port 228 of the laparoscope 202 can receive an inspection SWIR beam that can be transmitted by the laparoscope from the proximal end 220 to the distal end 222. In some implementations, visible-light beam and SWIR beam can travel along the same optical channel (e.g., an optical fiber, a waveguide, etc. in the laparoscope). The beam width of the visible-light beam and the inspection SWIR beam can vary. The inspection visible-light beam and the inspection SWIR beam can travel along the first optical path 242 (e.g., in the optical channel in the laparoscope) extending from the proximal end 220 to the distal end 222.

The inspection visible-light beam and/or inspection SWIR beam can interact with a target tissue and generate radiation that can be used to identify portions of the target tissue. For example, a detection visible-light beam is generated based on an interaction between the target tissue and at the inspection visible-light beam (or a portion thereof), and a detection SWIR beam can be generated based on an interaction between the target tissue and at least a portion of the inspection SWIR beam. The laparoscope can guide the detection visible-light beam and the detection SWIR beam along a second optical path 244 (e.g., in the optical channel in the laparoscope) extending from the distal end 222 to the proximal end 220. In some implementations, the first optical path 242 and the second optical path 244 are in the same optical channel. For example, the optical channel can include one or more rod lenses that can guide inspection visible-light beam and inspection SWIR beam from the proximal end 220 to the distal 222; and guide detection visible-light beam and detection SWIR beam from the distal end 222 to the proximal end 220). The detection visible-light beam and the detection SWIR beam can exit the laparoscope 202 via the second port 228.

In some embodiments, the first optical path 242 may comprise one or more fibers (e.g., a fiber bundle) and may form a peripheral optical path located in a radial peripheral region of the optical channel of the laparoscope. In some embodiments, a peripheral optical path may have an annular cross-section and may extend along the optical channel of the laparoscope. One or more fibers forming first optical path 242 may extend (individually and/or collectively) between first port 226 and output aperture 224, such that inspection light that is input into the laparoscope via first port 226 may propagate via first optical path 242 to output aperture 224.

In some embodiments, the second optical path 244 may comprise one or more rod lenses arranged in series with one another, and may form a central optical path located in a radial center region of the optical channel of the laparoscope. One or more rod lenses forming second optical path 244 may extend (individually and/or collectively) between second port 228 and output aperture 224, such that detection light that is input into the laparoscope via output aperture 224 may propagate via second optical path 244 to second port 228.

In some known systems, a laparoscope may be configured such that a peripheral path such as first optical path 242 may carry only inspection light, while a central path such as second optical path 244 may carry only detection light. However, in some embodiments, as disclosed herein, second optical path 244 may be used for both inspection light and detection light, in that it may carry inspection light from a light source, via second port 228, to output aperture 224 to be incident upon tissue; and it may also carry detection light from the tissue, via output aperture 224, to second port 228 to be incident upon a detector.

In some embodiments, using a central optical path such as second optical path 244 may have one or more advantages, including that a central optical path may transmit inspection light in such a manner that the polarization of the light is preserved to a greater degree than it would be preserved if it were transmitted via a peripheral optical path such as first optical path 242. For example, in embodiments in which a central optical path comprises a finite number of rod lenses (e.g., less than 10, less than 5, or less than 3 rod lenses) in series with one another, light propagating along the central optical path may arrive at an output aperture with its original polarization (at the point of input into the central optical path) largely preserved as compared to light propagating along a peripheral optical path. In some embodiments, preservation of polarization of light propagating a predefined distance along an optical path defined by a finite number of rod lenses may be greater than preservation of polarization of light propagating a predefined distance along an optical path defined by one or more fibers.

In some embodiments, light that propagates along the first optical path 242 between first port 226 and output aperture 224 may lose essentially all polarization. In some embodiments, the light may have a degree of polarization (DOP) of greater than or equal to 95%, 99%, or 99.9% upon entry into first optical path 242 via first port 226, and may have a DOP of less than or equal to 5%, 1%, or 0.1% upon exit from first optical path 242 via output aperture 224. In some embodiments, the DOP of light exiting the first optical path 242 may be less than or equal to 0.1%, 1%, or 5% of the DOP of light entering the first optical path 242. In some embodiments, one or more of these principles regarding preservation of polarization of light along first optical path 242 may be applicable to visible light, SWIR light, and/or to light traveling in either direction along the optical path.

In some embodiments, light that propagates along the second optical path 244 between second port 228 and output aperture 224 may lose essentially all polarization. In some embodiments, the light may have a degree of polarization (DOP) of greater than or equal to 95%, 99%, or 99.9% upon entry into second optical path 244 via second port 228, and may have a DOP of greater than or equal to 95%, 99%, or 99.9% upon exit from second optical path 244 via output aperture 224. In some embodiments, the DOP of light exiting the second optical path 244 may be greater than or equal to 95%, 99%, or 99.9% of the DOP of light entering the second optical path 244. In some embodiments, one or more of these principles regarding preservation of polarization of light along second optical path 244 may be applicable to visible light, SWIR light, and/or to light traveling in either direction along the optical path.

By ensuring that both inspection light and collection light can propagate through a laparoscope with the polarization in the laparoscope preserved, improved cross-polarization imaging (e.g., with improved surface penetration depth) using the laparoscope may be enabled. Accordingly, improved cross-polarization SWIR imaging may be enabled using system 200 to cause an inspection SWIR beam and a collection SWIR beam each to propagate along second optical path 244.

The optical system 204, includes a SWIR source coupling 230 that can allow the optical system 204 to couple to the SWIR source 214. For example, the optical system can receive an input SWIR beam from the SWIR source via the SWIR source coupling 230. As described in FIG. 3, the input SWIR beam can be modified by the optical system 204 and a portion thereof can be directed out of the optical system 204. For example, the inspection SWIR beam (which includes at least a portion of the input SWIR light beam or modifications thereof) can be directed out of the optical system 204 via a first port coupling 232 of the optical system 204.

The optical system 204 can include a visible-light sensor coupling 234 configured to couple to the visible-light sensor 216. A visible-light beam indicative of the detection visible-light beam can be directed out of the visible-light sensor coupling 234 and detected by the visible-light sensor 216. The optical system 204 can include a SWIR sensor coupling 236 configured to couple to the SWIR sensor 218. A SWIR beam indicative of the detection SWIR beam can be directed out of the SWIR sensor coupling 236 and detected by the SWIR sensor 218.

In operation, the inspection visible-light beam can enter the laparoscope 202 via the first port 226 and can be guided by an optical channel (e.g., optical fiber bundle) in the laparoscope 202 from the proximal end 220 to the distal end 222 (e.g., along the first optical path 242). The inspection visible-light beam exits the laparoscope via the output aperture 224 and interacts with a target tissue. A detection visible-light beam can enter the laparoscope 202 via the output aperture 224 and can be guided by the optical channel in the laparoscope from the distal end 222 to the proximal end 220 (e.g., along the second optical path 244), and exit the laparoscope via the second port 228.

In operation, the inspection SWIR beam can enter the laparoscope via the second port 228, and can be guided by an optical channel in the laparoscope from the proximal end 220 to the distal end 222 (e.g., along the first optical path 242). The inspection SWIR beam exits the laparoscope 202 via the output aperture 224 and interacts with a target tissue. A detection SWIR beam can enter the laparoscope 202 via the output aperture 224 and can be guided by the optical channel in the laparoscope 202 from the distal end 222 to the proximal end 220 (e.g., along the second optical path 244), and exit the laparoscope via the second port 228.

The imaging system 200 ("single accessory design") can allow for visible-light imaging, SWIR imaging or a combination thereof of a target tissue using existing laparoscopes. For example, existing laparoscope that have an optical channel that can support transmission of both visible-light beam and SWIR beam (e.g., when the optical channel is an optical fiber with sufficiently large diameter to support visible-light beam and SWIR beam) can be used for both visible-light imaging and SWIR-imaging. Imaging using both the visible-light and the SWIR can improve the contrast of the image of the target tissue. Moreover, the visible-light and/or SWIR imaging can be achieved by retrofitting the optical system 204 on to existing laparoscope (e.g., by attaching optical system 204 to a port of the laparoscope) without redesigning the laparoscope. This can allow a user (e.g., a physician) to perform both types of imaging without changing the laparoscope (e.g., inserting a new laparoscope into the body during an operation).

Figure 3:
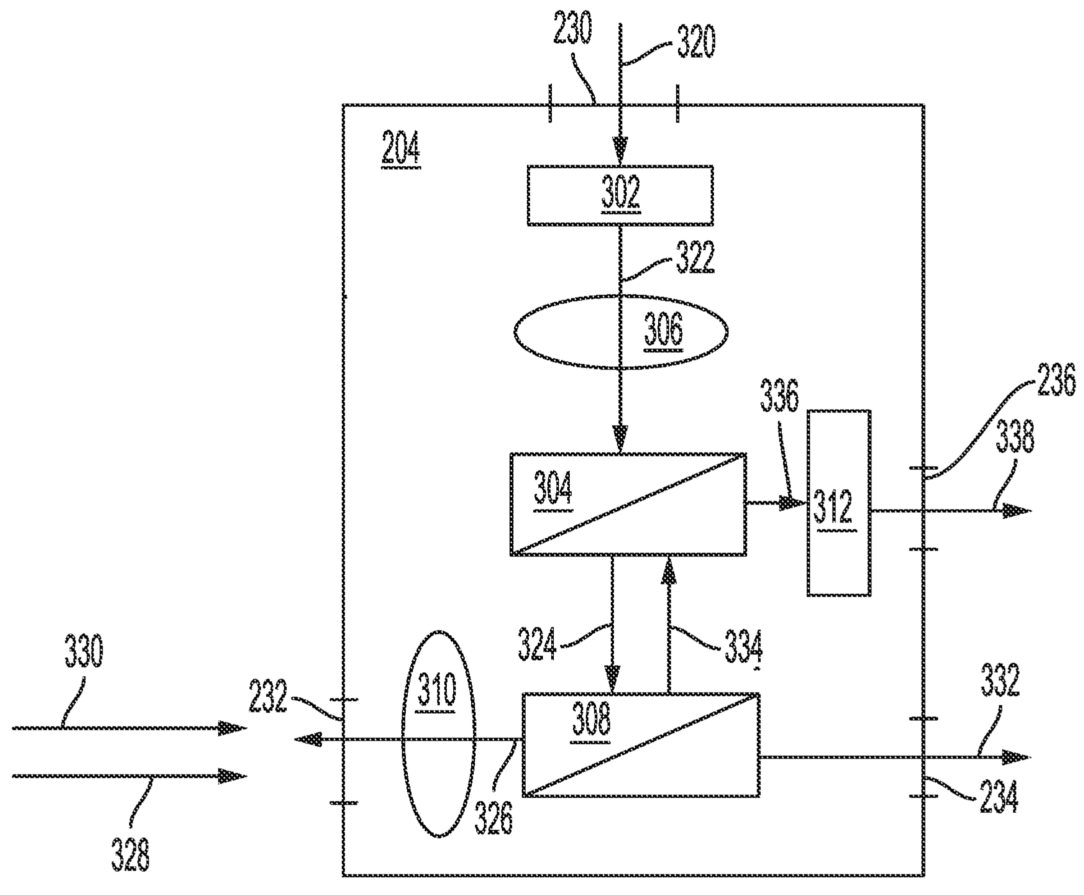
FIG. 3 illustrates an implementation of an optical system in the SWIR imaging system of FIG. 2.

FIG. 3 illustrates an example implementation of the optical system 204 that includes a first polarizer 302, a first optical element 304 and a second optical element 308. The first polarizer 302 can be configured to receive the input SWIR beam 320 (e.g., from the SWIR source 214 via SWIR source coupling 230) and transmit a first SWIR beam 322. The first polarizer 302 is configured such that the first SWIR beam 322 has a first polarization. For example, the first polarizer 302 can select a portion of the input SWIR beam 320 that has the first polarization, and transmit it as the first SWIR beam 322. The first optical element 304 can be located downstream (along the optical path of the first SWIR beam 322) from the first polarizer 302, and can receive the first SWIR beam 322.

In some implementations, the first optical element 304 can be a polarization beam splitter that can transmit radiation of a first predetermined polarization, and reflect radiation of a second predetermined polarization. The first optical element 304 can be configured (e.g., oriented) to allow radiation having the first polarization transmitted. For example, the first optical element 304 can transmit the first SWIR beam 322 (or a portion thereof) that has the first polarization. A second SWIR beam 324 transmitted by the first optical element 304 can include the portion of the first SWIR beam 322 that has the first polarization. In some implementations, a focusing lens 306 can be placed between the first polarizer 302 and the first optical element 304. The focusing lens 306 can collimate the first SWIR beam 322.

The transmitted second SWIR beam 324 can be received by a second optical element 308. The second optical element 308 (e.g., a dichoric mirror, a beam splitter) can be configured to reflect radiation having a first range of wavelengths, and transmit radiation having a second range of wavelengths. For example, the second optical element 308 can reflect the second SWIR beam 324 (or a portion thereof). The inspection SWIR beam 326 that is directed out of the optical system 204 via the first port coupling 232 can include the reflected portion of the second SWIR beam 324. As described in FIG. 2, the inspection SWIR beam 326 can be received by the second port 228 of the laparoscope 202.

The second optical element 308 can receive the detection visible-light beam 328 and the detection SWIR beam 330 via the first port coupling 232 and the second port 228. The second optical element 308 can transmit the detection visible-light beam 328 (or a portion thereof). For example, a first visible-light beam 332 that includes at least a portion of the detection visible-light beam 328 can be transmitted by optical element 308. The detection visible-light beam 328 can have a wavelength that falls within the second range of wavelengths that are transmitted by the second optical element 308. The second optical element 308 can reflect the detection SWIR beam 330. For example, a third SWIR beam 334 that includes at least a portion of the detection SWIR beam 330 can be reflected by optical element 308. The detection SWIR beam 328 can have a wavelength that falls within the first range of wavelengths that are reflected by the second optical element 308 (e.g., a dichoric mirror, a beam splitter, etc.).

The first optical element 304 can be configured to receive the third SWIR beam 334 and reflect at least a portion thereof. A fourth SWIR beam 336 that includes the reflected portions of the third SWIR beam 334 is directed away from the first optical element 304. As described above, in some implementations, the first optical element 304 can be a polarization beam splitter configured to reflect radiation having a second polarization. In this implementation, the fourth SWIR beam 336 can include the portion of the third SWIR beam 334 that has the second polarization. Alternately, the first optical element can be an intensity beam splitter (e.g., 50-50 beam splitter, 90-10 beam splitter)

In some implementations, the second polarizer 312 can receive the fourth SWIR beam 336 and transmit at least a portion of the fourth SWIR beam 336. For example, the second polarizer 312 can be configured to transmit a fifth SWIR radiation 338 having the second polarization. In some implementations, the first polarizer 302 and the second polarizer 312 can be oriented relative to each other. For example, a user can rotate the first polarizer 302 and/or second polarizer 312 (e.g., around their respective optical axes defined by propagation direction of the first SWIR beam 322 [for first polarizer 302] and fifth SWIR beam 338 [for second polarizer 312]). Rotating the first polarizer 302 and/or second polarizer 312 can reduce the glare in the image of the target tissue obtained from detection SWIR beam. Additionally or alternately, rotating the first polarizer 302 and/or second polarizer 312 can increase the penetration depth of the portion of target tissue being imaged by the SWIR beam. Such a configuration of the first polarizer 302 and the second polarizer 312 can be used when the first optical element 304 is an intensity beam splitter (e.g., 50-50 beam splitter, 90-10 beam splitter, etc.). In some implementations, having using a pair of orthogonal polarizers can improve the performance of the optical system 204 (e.g., allow for tuning of polarization that can result in improved imaging of the target tissue). In some implementations, the optical system 204 may not include polarizers (e.g., first polarizer 302, second polarizer 312, etc.). For example, first polarizer 302 and/or second polarizer 312 may not be included in the optical system 204.

In some implementations, the optical channel in the laparoscope 202 can transmit both the inspection and the detection visible-light/SWIR beams without scrambling their polarization (e.g., without depolarizing the beams). In other words, the inspection visible-light/SWIR beams and the detection visible-light/SWIR beam may maintain their polarization (or a portion thereof) during transmission through the optical channel. This can allow for application of cross-polarization imaging techniques that can result in improved imaging of the target tissue. For example, if the inspection beam has a first linear polarization (which is maintained as the inspection beam is transmitted through the optical channel), a portion of the detection beam that has a second linear polarization perpendicular to the first linear polarization can be detected/imaged (e.g., by visible-light detector 216 for visible-light detection beam, by SWIR detector 218 for SWIR detection beam, etc.). This can be achieved by placing a polarizer configured to transmit the second linear polarization upstream from the visible-light detector 216/SWIR detector 218.

Cross-polarization imaging can allow for imaging of portions of the target tissue away from the surface of the target tissue (e.g., at a depth relative to the surface of the target tissue). For example, the surface of the target tissue can generate a first portion of the detection beam that has the same polarization as the inspection beam (e.g., first linear polarization) based on reflection of the inspection beam (or a portion thereof). However, the portion of the target tissue away from the surface may generate a randomly polarized light. For example, the target tissue can be highly scattering, and can depolarize a linearly polarized light beam (e.g., portion of inspection beam that has entered into the target tissue). A portion of the randomly polarized light can have a second linear polarization. Imaging the portion of the detection beam having the second polarization while filtering out the portion of the detection beam having the first polarization can improve the imaging of the portion of the target tissue away from the surface of the target tissue. This can be useful for imaging lymph nodes that are surrounded by other tissues.

Below, FIGS. 4 and 5 describe some embodiments of imaging systems and components thereof for laparoscopic imaging. In particular, the systems described may enable cross-polarization SWIR imaging using one or more accessories that may be attached to two ports of a laparoscope. The one or more accessories may use a first set of one or more optical elements (e.g., beam-splitters, dichroic mirrors, etc.) to splice together a SWIR inspection beam and a visible-light inspection beam and to direct both beams into a first port of the laparoscope and into a peripheral optical path of the laparoscope. The one or more accessories may use second set of one or more optical elements (e.g., beam-splitters, dichroic mirrors, etc.) to collect both a SWIR detection beam and a visible-light detection beam from the central optical path of the laparoscope via a second port of the laparoscope, and to split the beams from one another such that they are directed to respective optical sensors configured for the respective wavelengths.

Figure 4:
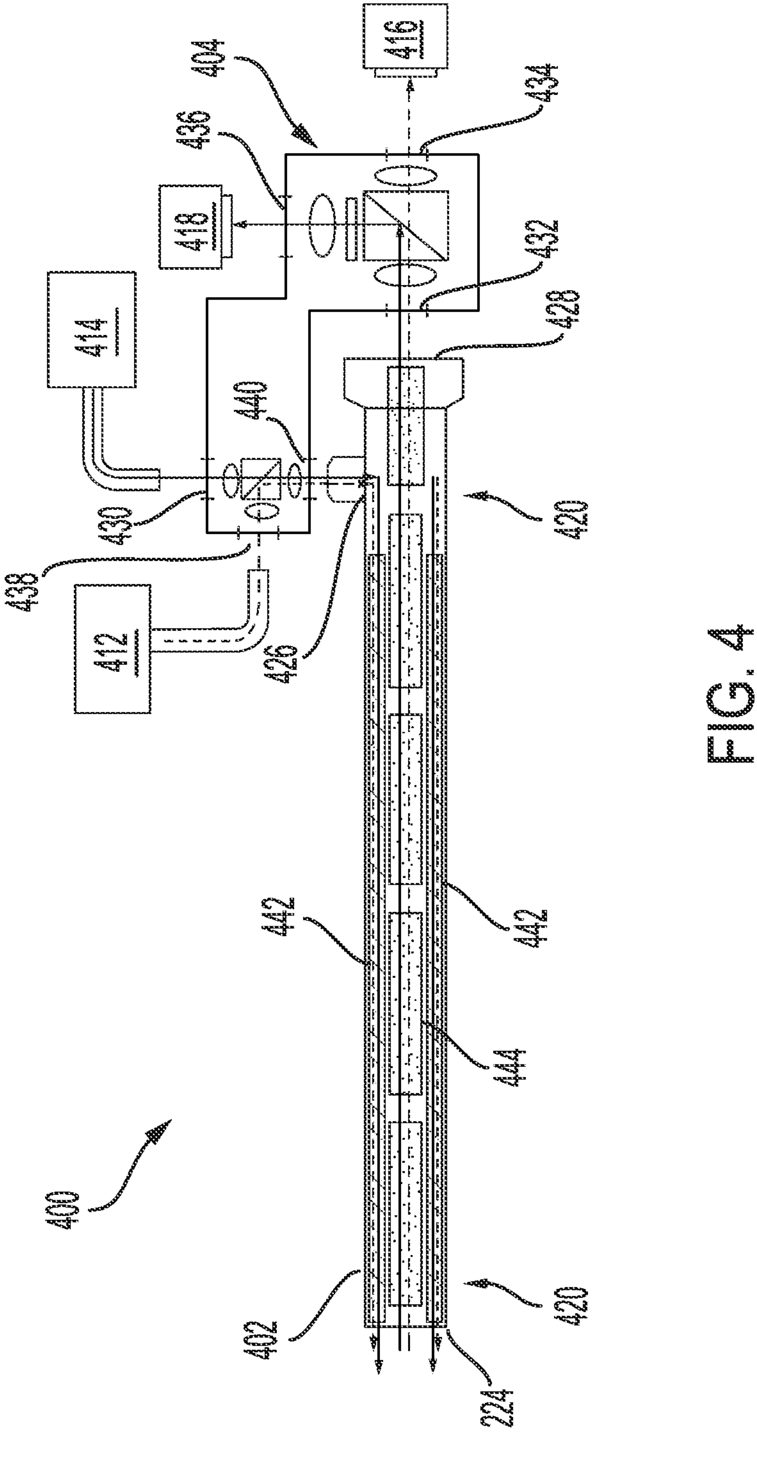
FIG. 4 illustrates another exemplary embodiment of a SWIR imaging system.

In some embodiments, any one or more components shown or described in FIGS. 4 and/or 5 may share any one or more features in common with corresponding components shown or described in FIGS. 2 and/or 3.

FIG. 4 illustrates an exemplary embodiment of an imaging system 400. The imaging system 400 includes a laparoscope 402 and an optical system 404. The imaging system 400 can be optically coupled with a visible-light source 412 and a SWIR source 414. The imaging system 400 can also be optically coupled to visible-light detector 416 and SWIR detector 418. The laparoscope 400 can guide inspection beams (e.g., visible-light beam, SWIR beams, etc.) that can exit via an output aperture 424 of the laparoscope 400.

The laparoscope 400 can include a first port 426 and a second port 428. The first port 426 of the laparoscope 400 can receive an inspection visible-light beam and an inspection SWIR light beam from the optical system 404. The inspection visible-light beam and the inspection SWIR beam (or a portion thereof) can be transmitted by the laparoscope from the proximal end 420 to the distal end 422 (along a first optical path 442 in the laparoscope 402). In some implementations, both the SWIR and visible-light beam are transmitted on the same (e.g., shared) optical path (e.g., first optical path 442 in the laparoscope 402).

The inspection visible-light beam and/or inspection SWIR beam can interact with a target tissue and generate radiation that can be used to identify portions of the target tissue. For example, a detection visible-light beam can be generated based on an interaction between the target tissue and at the inspection visible-light (or a portion thereof), and a detection SWIR beam can be generated based on an interaction between the target tissue and at least a portion of the inspection SWIR beam. The laparoscope 402 can guide the detection visible-light beam and the detection SWIR beam from the distal end 422 to the proximal end 420 (along a second optical path 444 in the laparoscope 402). The detection visible-light beam and the detection SWIR beam can exit the laparoscope 402 via the second port 428.

The optical system 404 can include a SWIR source coupling 430 that can allow the optical system 404 to couple to the SWIR source 414. For example, the optical system 404 can receive an input SWIR beam from the SWIR source via the SWIR source coupling 430. As described in FIG. 5, the input SWIR beam can be modified by the optical system 404 and a portion thereof can be directed out of the optical system 404. For example, the inspection SWIR beam (which includes at least a portion of the input SWIR light beam or modifications thereof) can exit via a second port coupling 440 of the optical system 404.

The optical system 404 can include a visible-light source coupling 438 that can allow the optical system 404 to couple to the visible-light source 412. For example, the optical system 404 can receive an input visible-light beam from the visible-light source 412 via the visible-light source coupling 438. As described in FIG. 5, the input visible-light beam can be modified by the optical system 404 and a portion thereof can be directed out of the optical system 404. For example, the inspection visible-light beam (which includes at least a portion of the input visible-light beam or modifications thereof) can exit via the second port coupling 440 of the optical system 404.

The optical system 404 includes a visible-light sensor coupling 434 configured to optically couple to the visible-light sensor 416. A visible-light beam indicative of the detection visible-light beam can be directed out of the visible-light sensor coupling 434 and detected by the visible-light sensor 416. The optical system 404 includes a SWIR sensor coupling 436 configured to couple to the SWIR sensor 418. A SWIR beam indicative of the detection SWIR beam can be directed out of the SWIR sensor coupling 436 and detected by the SWIR sensor 418.

In operation, the inspection visible-light beam can enter the laparoscope 402 via the first port 426 and can be guided by a first optical channel in the laparoscope 402 from the proximal end 420 to the distal end 422 (e.g., along the first optical path 442). The inspection visible-light beam exits the laparoscope 402 via the output aperture 424 and interacts with a target tissue. A detection visible-light beam can enter the laparoscope via the output aperture 424 and can be guided by a second optical channel in the laparoscope 402 from the distal end 422 to the proximal end 420 (e.g., along the second optical path 444), and exit the laparoscope via the second port 428.

In operation, the inspection SWIR beam can enter the laparoscope via the first port 426, and can be guided by the first optical channel in the laparoscope 402 from the proximal end 420 to the distal end 422 (e.g., along the first optical path 442). The inspection SWIR beam exits the laparoscope via the output aperture 424 and interacts with a target tissue. A detection SWIR beam can enter the laparoscope 402 via the output aperture 424 and can be guided by the second optical channel in the laparoscope from the distal end 422 to the proximal end 420 (e.g., along the second optical path 444), and exit the laparoscope via the second port 428. In some implementations, the first optical channel can include an optical fiber bundle (e.g., located in a peripheral portion of the laparoscope), and the second optical channel can include one or more rod lenses (e.g., located in the central portion of the laparoscope).

Figure 5:
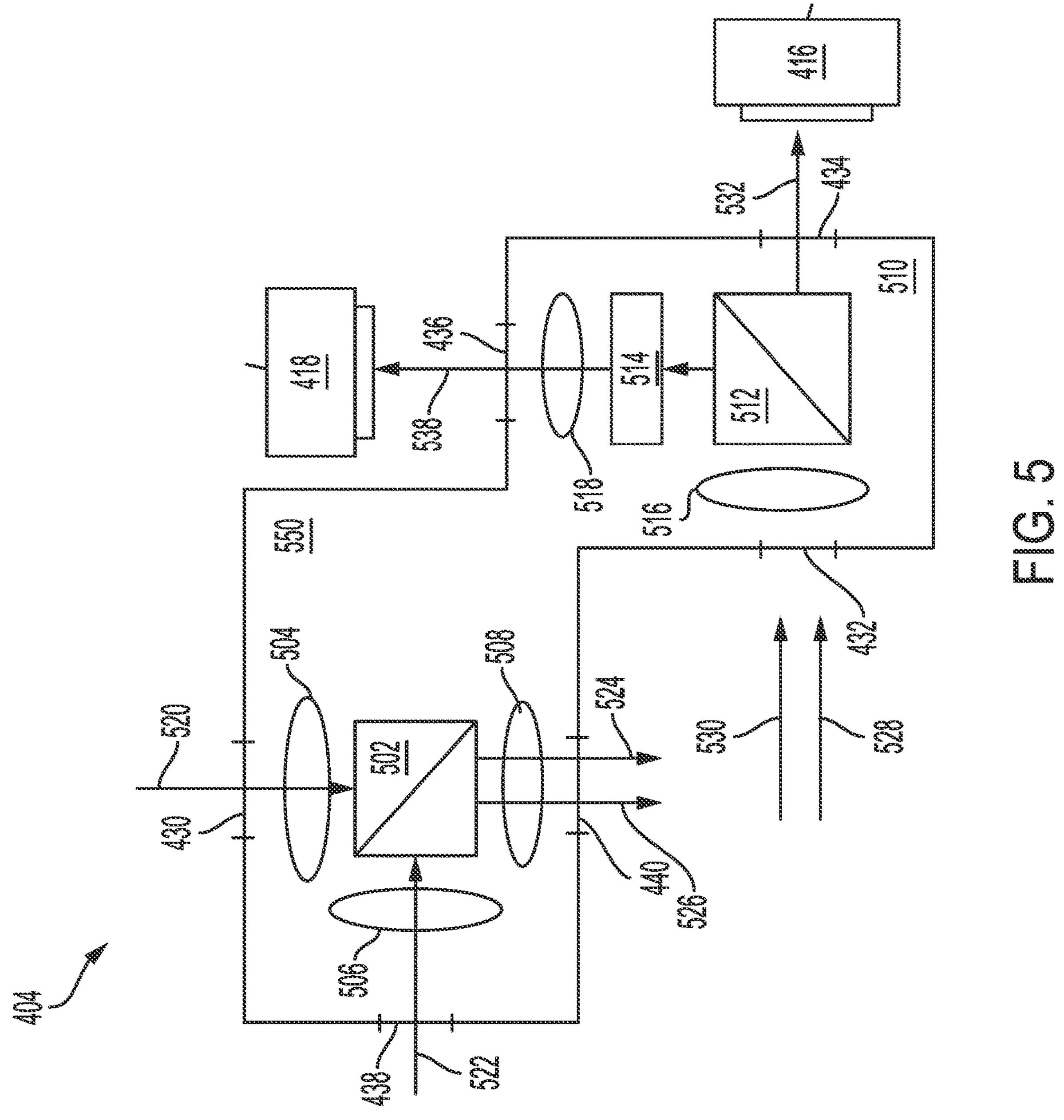
FIG. 5 illustrates an implementation of an optical system in the SWIR imaging system of FIG. 4.

FIG. 5 illustrates an implementation of the optical system 404 that includes a detection sub-system 510 and an inspection sub-system 550. In some embodiments, detection sub-system 510 and inspection sub-system 550 may be provided as physically separate sub-systems from one another (e.g., as two separate accessories configured to be independently attachable and detachable from respective ports of a laparoscope); in some embodiments, detection sub-system 510 and inspection sub-system 550 may be provided as parts of a single physical system (e.g., as a single accessory that is attachable to multiple ports of a laparoscope). The inspection sub-system 550 can be optically coupled to the first port 426 of the laparoscope 402 via the second port coupling 440. An optical element 502 (e.g., a dichoric mirror, a beam splitter, etc.) in the inspection sub-system 550 can be configured to reflect radiation having a first set of wavelengths, and transmit radiation having a second set of wavelengths. The optical element 502 can be configured to receive the input SWIR beam 520 (e.g., from the SWIR source 414 via SWIR source coupling 430) and transmit at least a portion thereof. For example, an inspection SWIR beam 524 that includes at least a portion of the input SWIR beam 520 can be transmitted by optical element 502. The input SWIR beam can have a wavelength that falls within the second set of wavelengths that are transmitted by the optical element 502. In some implementations, a first focusing lens 504 can be placed upstream from the first optical element 502 and in the path of input SWIR beam 520. The first focusing lens 504 can collimate the input SWIR beam 520.

The optical element 502 can be configured to receive an input visible-light beam 522 (e.g., from the visible-light source 412 via visible-light source coupling 438) and reflect at least a portion thereof. For example, an inspection visible-light beam 526 that includes at least a portion of the input visible-light beam 522 can be reflected by optical element 502. The input visible-light beam can have a wavelength that falls within the first set of wavelengths that are reflected by the optical element 502. In some implementations, a second focusing lens 506 can be placed upstream from the first optical element 502 and in the path of input visible-light beam 522. The second focusing lens 504 can collimate the first visible-light beam 522.

The optical system 404 can include the detection sub-system 510 coupled to the second port 428 of the laparoscope. The detection sub-system 510 can include an optical element 512 (e.g., a dichoric mirror, a beam splitter, etc.) that can be configured to reflect radiation having a first range of wavelengths, and transmit radiation having a second range of wavelengths. The optical element 512 can be configured to receive detection visible-light beam 528 and the detection SWIR beam 530 (e.g., via the first port coupling 432 and the second port 428). The optical element 512 can transmit the detection visible-light beam 528 (or a portion thereof). For example, a first visible-light beam 532 that includes at least a portion of the detection visible-light beam 528 can be transmitted by optical element 512. The detection visible-light beam 528 can have a wavelength that falls within the second range of wavelengths that are transmitted by the optical element 512. The first visible-light beam 532 can be directed out of the detection optical sub-system 510 via the visible-light sensor coupling 434 and can be detected by the visible-light detector 416.

The optical element 512 can reflect the detection SWIR beam 530. For example, a first SWIR beam 534 that includes at least a portion of the detection SWIR beam 530 can be directed away from the optical element 512. The detection SWIR beam 528 can have a wavelength that falls within the first range of wavelengths that are reflected by the optical element 512. In some implementations, a focusing lens 516 ("relay lens") can be placed upstream from the optical element 512 and in the path of detection visible-light beam 528 and detection SWIR beam 530. In some implementations, the focusing lens 516 can collimate both of the detection SWIR beam and the detection visible-light beam before they impinge on the optical element 512. The focusing lens 516 can collimate the inspection detection beam before it enters the laparoscope 402.

In some implementations, a polarizer 514 can receive the first SWIR beam 534 and transmit at least a portion of the first SWIR beam 534. For example, the polarizer 514 can be configured to transmit a portion of the first SWIR radiation 534 having a predetermined polarization. In some implementations, polarizer 514 can allow for application of cross-polarization imaging techniques described above (e.g., by configuring the polarizer 514 to transmit a portion of the detection SWIR beam with polarization perpendicular to the polarization of the inspection SWIR beam). Alternately, polarizer 514 can reduce glare (e.g., by attenuating portions of the detection SWIR beam having undesirable polarization). A second SWIR beam 538 including the portion of the first SWIR beam 534 having the predetermined polarization is transmitted by the polarizer 514. The second SWIR beam 538 can be directed out of the detection optical sub-system 510 via the SWIR sensor coupling 436 and can be detected by the SWIR detector 418. A focusing lens 518 can be placed downstream from the polarizer 514 and in the path of the second SWIR beam 538. The focusing lens 518 can collimate the second SWIR beam 538.

The imaging system 400 ("two accessory design") can allow for visible-light imaging, SWIR imaging or a combination thereof of a target tissue using existing laparoscopes. For example, existing laparoscope that have an optical channel that can support transmission of both visible-light beam and SWIR beam (e.g., when the optical channel is an optical fiber with sufficiently large diameter to support visible-light beam and SWIR beam) can be used for both visible-light imaging and SWIR-imaging. Imaging using both the visible-light and the SWIR can improve the contrast of the image of the target tissue. Moreover, the visible-light and/or SWIR imaging can be achieved by retrofitting the optical system 404 on to existing laparoscope (e.g., by attaching optical system 404 to a port of the laparoscope) without redesigning the laparoscope. This can allow a user (e.g., a physician) to perform both types of imaging without changing the laparoscope (e.g., inserting a new laparoscope into the body during an operation). In some implementations, the detection sub-system 510 and the inspection sub-system 550 can be separate units that can be individually attached to the laparoscope 402 ("two-accessory design"). A surgeon can separately attach the two sub-systems to the different ports of the laparoscope 402 (e.g., inspection sub-system 550 to the first port 426 and detection sub-system 510 to second port 428).

Certain exemplary embodiments will now be described to provide an overall understanding of the principles of the structure, function, manufacture, and use of the systems, devices, and methods disclosed herein. One or more examples of these embodiments are illustrated in the accompanying drawings. Those skilled in the art will understand that the systems, devices, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention. Further, in the present disclosure, like-named components of the embodiments generally have similar features, and thus within a particular embodiment each feature of each like-named component is not necessarily fully elaborated upon.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine-readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub-programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application-specific integrated circuit).

Processors suitable for the execution of a computer program include, by way of example, both general and special purpose microprocessors, and any one or more processor of any kind of digital computer. Generally, a processor will receive instructions and data from a Read-Only Memory or a Random Access Memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. Information carriers suitable for embodying computer program instructions and data include all forms of non-volatile memory, including by way of example semiconductor memory devices, (e.g., EPROM, EEPROM, and flash memory devices); magnetic disks, (e.g., internal hard disks or removable disks); magneto-optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The techniques described herein can be implemented using one or more modules. As used herein, the term "module" refers to computing software, firmware, hardware, and/or various combinations thereof. At a minimum, however, modules are not to be interpreted as software that is not implemented on hardware, firmware, or recorded on a non-transitory processor readable recordable storage medium (i.e., modules are not software per se). Indeed "module" is to be interpreted to always include at least some physical, non-transitory hardware such as a part of a processor or computer. Two different modules can share the same physical hardware (e.g., two different modules can use the same processor and network interface). The modules described herein can be combined, integrated, separated, and/or duplicated to support various applications. Also, a function described herein as being performed at a particular module can be performed at one or more other modules and/or by one or more other devices instead of or in addition to the function performed at the particular module. Further, the modules can be implemented across multiple devices and/or other components local or remote to one another. Additionally, the modules can be moved from one device and added to another device, and/or can be included in both devices.

The subject matter described herein can be implemented in a computing system that includes a back-end component (e.g., a data server), a middleware component (e.g., an application server), or a front-end component (e.g., a client computer having a graphical user interface or a web interface through which a user can interact with an implementation of the subject matter described herein), or any combination of such back-end, middleware, and front-end components. The components of the system can be interconnected by any form or medium of digital data communication, e.g., a communication network. Examples of communication networks include a local area network ("LAN") and a wide area network ("WAN"), e.g., the Internet.

Approximating language, as used herein throughout the specification and claims, may be applied to modify any quantitative representation that could permissibly vary without resulting in a change in the basic function to which it is related. Accordingly, a value modified by a term or terms, such as "about" and "substantially," are not to be limited to the precise value specified. In at least some instances, the approximating language may correspond to the precision of an instrument for measuring the value. Here and throughout the specification and claims, range limitations may be combined and/or interchanged, such ranges are identified and include all the sub-ranges contained therein unless context or language indicates otherwise.

Following is a list of exemplary embodiments, which may in some embodiments be combined in whole or in part with one another and/or with any of the other features or embodiments described herein:

What is claimed is:

1. A system comprising:

a laparoscope including a first port and a second port;

an optical system comprising a first port coupling, a shortwave infrared (SWIR) sensor coupling configured to couple to a SWIR sensor, and a visible-light sensor coupling configured to couple to a visible-light sensor, wherein the optical system is configured to optically couple to at least the second port of the laparoscope via the first port coupling, wherein the optical system is configured to receive a detection SWIR beam from the second port and direct at least a portion of the detection SWIR beam to the SWIR sensor coupling, and wherein the optical system is further configured to receive a detection visible-light beam from the second port and direct at least a portion of the detection visible-light beam to the visible-light sensor coupling, wherein the laparoscope is configured to receive an inspection visible-light beam via the first port, and an inspection SWIR beam via one of the first port and the second port; and wherein the optical system further includes:

a SWIR source coupling configured to couple to a SWIR source and receive the inspection SWIR beam via the SWIR source coupling;

a first polarizer configured to receive the inspection SWIR beam, and transmit a polarized portion of the inspection SWIR beam having a first polarization;

a first optical element downstream from the first polarizer and configured to receive the inspection SWIR beam and transmit at least a portion of the inspection SWIR beam having the first polarization;

a second optical element configured to receive the inspection SWIR beam and reflect at least a portion of the inspection SWIR beam out of the optical system via the first port coupling and the second port of the laparoscope;

wherein the second optical element is configured to receive the detection visible-light beam and the detection SWIR beam via the first port coupling and the second port, transmit at least a portion of the detection visible-light beam, and reflect at least a portion of the detection SWIR beam.

2. The system of claim 1, wherein the detection visible-light beam is generated based on an interaction between a target tissue and at least a portion of the inspection visible-light, and wherein the detection SWIR beam is generated based on an interaction between the target tissue and at least a portion of the inspection SWIR beam.

3. The system of claim 1, wherein the first optical element is configured to receive the detection SWIR beam reflected by the second optical element, and reflect at least a portion of the detection SWIR beam having a second polarization.

4. The system of claim 3, further including a second polarizer configured to receive the detection SWIR beam reflected by the first optical element, and transmit at least a portion of the detection SWIR beam having the second polarization.

5. The system of claim 4, wherein the detection SWIR beam is directed from the second polarizer out of the optical system via the SWIR sensor coupling.

6. The system of claim 1, wherein the detection visible-light beam is directed from the second optical element out of the optical system via the visible-light sensor coupling.

7. The system of claim 1, wherein the inspection SWIR beam and the detection SWIR beam have a wavelength between 0.9 microns and 2 microns.

8. The system of claim 1, wherein the optical system includes:

a second port coupling configured to couple to the first port of the laparoscope; and a visible-light source coupling configured to couple to a visible-light source, and receive the inspection visible-light beam via the visible-light source coupling.

9. The system of claim 1, wherein the laparoscope includes:

a first optical path configured to optically couple the first port with an output aperture of the laparoscope, wherein the inspection visible-light beam and the inspection SWIR beam are configured to travel along the first optical path; and a second optical path configured to optically couple the output aperture with the second port, wherein detection visible-light beam and the detection SWIR beam are configured to travel along the second optical path.

10. A system comprising:

a laparoscope including a first port and a second port;

an optical system comprising a first port coupling, a shortwave infrared (SWIR) sensor coupling configured to couple to a SWIR sensor, and a visible-light sensor coupling configured to couple to a visible-light sensor, wherein the optical system is configured to optically couple to at least the second port of the laparoscope via the first port coupling, wherein the optical system is configured to receive a detection SWIR beam from the second port and direct at least a portion of the detection SWIR beam to the SWIR sensor coupling, and wherein the optical system is further configured to receive a detection visible-light beam from the second port and direct at least a portion of the detection visible-light beam to the visible-light sensor coupling, wherein the laparoscope is configured to receive an inspection visible-light beam via the first port, and an inspection SWIR beam via one of the first port and the second port; and wherein the optical system further includes:

a SWIR source coupling configured to couple to a SWIR source and receive the inspection SWIR beam via the SWIR source coupling;

a second port coupling configured to couple to the first port of the laparoscope;

a visible-light source coupling configured to couple to a visible-light source, and receive the inspection visible-light beam via the visible-light source coupling; and a first optical sub-system coupled to the second port of the laparoscope, the first optical sub-system including:

a first optical element configured to receive the detection visible-light beam and the detection SWIR beam via the first port coupling and the second port, transmit at least a portion of the detection visible-light beam, and reflect at least a portion of the detection SWIR beam; and a polarizer configured to receive the detection SWIR beam reflected by the first optical element and transmit at least a portion of the detection SWIR beam having a first polarization.

11. The system of claim 10, wherein detection SWIR beam is directed from the polarizer out of the first optical sub-system via the SWIR sensor coupling.

12. The system of claim 10, wherein at least a portion of the detection visible-light beam is directed from the first optical element out of the first optical sub-system via the visible-light sensor coupling.

13. The system of claim 10, wherein the optical system includes a second optical sub-system coupled to the first port of the laparoscope and including a second optical element, wherein the second optical element is configured to receive the inspection visible-light beam via the visible-light source coupling and reflect at least a portion of the inspection visible-light beam, wherein the inspection visible-light beam is directed out of the second optical sub-system via the second port coupling and the first port of the laparoscope.

14. The system of claim 13, wherein the second optical element is configured receive the inspection SWIR beam via the SWIR source coupling and transmit at least a portion of the inspection SWIR beam, wherein the inspection SWIR beam is directed from the second optical element out of the second optical system sub-system via the second port coupling and enters the laparoscope via the first port.

15. A system comprising:

a laparoscope including a first port and a second port;

an optical system comprising a first port coupling, a shortwave infrared (SWIR) sensor coupling configured to couple to a SWIR sensor, and a visible-light sensor coupling configured to couple to a visible-light sensor, wherein the optical system is configured to optically couple to at least the second port of the laparoscope via the first port coupling, wherein the optical system is configured to receive a detection SWIR beam from the second port and direct at least a portion of the detection SWIR beam to the SWIR sensor coupling, and wherein the optical system is further configured to receive a detection visible-light beam from the second port and direct at least a portion of the detection visible-light beam to the visible-light sensor coupling, wherein the laparoscope is configured to receive an inspection visible-light beam via the first port, and an inspection SWIR beam via one of the first port and the second port; and wherein the laparoscope further includes:

a first optical path configured to optically couple the first port with an output aperture of the laparoscope, wherein the inspection visible-light beam is configured to travel along the first optical path; and a second optical path configured to optically couple the output aperture with the second port, wherein the inspection SWIR beam, the detection visible-light beam, and the detection SWIR beam are configured to travel along the second optical path.

* * * * *